United States Patent [19]

Ludvigsen

[11] Patent Number: 5,236,664
[45] Date of Patent: Aug. 17, 1993

[54] APPARATUS FOR MONITORING BLOOD LOSS

[75] Inventor: Bernhard Ludvigsen, Mobile, Ala.

[73] Assignee: University of South Alabama, Mobile, Ala.

[21] Appl. No.: 861,102

[22] Filed: Mar. 31, 1992

Related U.S. Application Data

[63] Continuation-in-part of Ser. No. 681,896, Apr. 8, 1991.

[51] Int. Cl.$^5$ .............................................. A61B 5/00
[52] U.S. Cl. ...................................... 422/44; 422/20; 422/68.1; 422/82.03; 436/66; 128/638; 210/748; 356/40; 204/416
[58] Field of Search ........................ 436/66, 155, 177; 422/20, 44, 62, 82.03, 68.1; 128/637, 638; 435/2, 288; 210/646, 748; 356/40; 204/416

[56] References Cited

U.S. PATENT DOCUMENTS

| | | | |
|---|---|---|---|
| 3,492,095 | 1/1970 | Tillen | 23/230 |
| 3,874,850 | 4/1975 | Sorensen et al. | 356/40 X |
| 3,972,614 | 8/1976 | Johansen et al. | 356/40 X |
| 4,193,818 | 3/1980 | Young et al. | 422/128 X |
| 4,428,800 | 1/1984 | Tarcy | 436/124 X |
| 4,562,842 | 1/1986 | Morfeld et al. | 128/638 |
| 4,766,080 | 8/1988 | Fleming | 436/164 X |
| 4,773,423 | 9/1988 | Hakky | 128/637 |
| 4,853,338 | 8/1989 | Benezra et al. | 436/66 |
| 4,876,205 | 10/1989 | Green et al. | 436/66 |
| 5,087,379 | 2/1992 | Morton et al. | 210/748 |

*Primary Examiner*—James C. Housel
*Assistant Examiner*—Maureen M. Wallenhorst
*Attorney, Agent, or Firm*—Oblon, Spivak, McClelland, Maier & Neustadt

[57] ABSTRACT

A blood loss monitoring apparatus is disclosed. The system includes a tank having a solution which removes blood from blood containing materials which are deposited in the tank and also hemolyzes the blood. Blood and blood containing materials are deposited into the tank during surgery, and the volume of liquid in the tank as well as the hemoglobin concentration in the tank are then determined. From this information, the total amount of hemoglobin lost is determined, and by measuring the patient's hemoglobin level immediately prior to the surgery, the total amount of blood lost is then calculated. The amount of blood lost can be continuously monitored and updated throughout the course of the surgical procedure or operation.

20 Claims, 4 Drawing Sheets

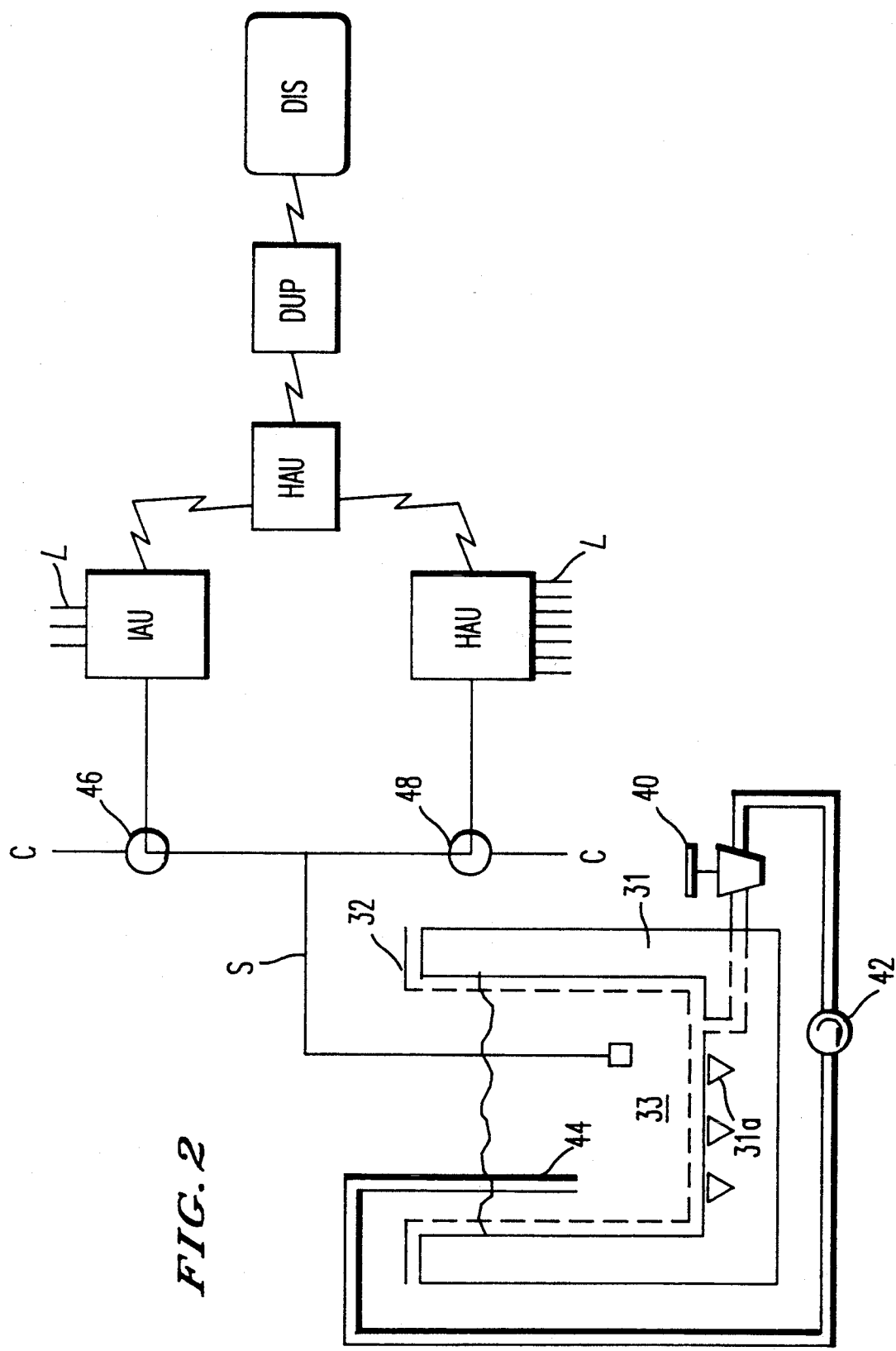

APPARATUS FOR MONITORING BLOOD LOSS

RELATED APPLICATION

This application is a continuation-in-part of U.S. Application Ser. No. 07/681,896 filed Apr. 8, 1991 which is incorporated herein by reference.

BACKGROUND OF THE INVENTION

1. Field of the Invention

The invention provides an apparatus for determining blood loss in a patient, particularly a patient undergoing an operation, such that the need for and amount of a blood transfusion can be determined. The blood loss monitor is envisioned primarily for use with human patients, but also may be utilized for other animals, particularly in research. In accordance with the present invention, the amount of blood lost during a surgical procedure can be substantially continuously monitored as the operation or procedure progresses.

2. Discussion of the Background

During a surgical operation or procedure, it is extremely important to determine the amount of blood lost by the patient. In particular, it is important to avoid the use of a blood transfusion when unnecessary, to conserve blood supplies and also to avoid potential risks to the patient associated with exposure to blood which may contain contaminants or undetected viruses. However, where the blood loss is significant, a transfusion must be utilized to ensure the patient's well-being.

Often it is difficult to determine the precise amount of blood loss during an operation. For example, where the surgeon or anesthesiologist are tending to other matters, it is difficult to concentrate on the amount of blood lost, particularly during operations which involve large blood losses. In addition, mere visual observation is typically inaccurate. Nevertheless, transfusion practices often vary, and frequently are based upon a subjective assessment by the physician. In the past, physicians have often utilized a liberal approach to transfusions, with the philosophy that it is better to "stay ahead" than lag behind with regard to the patient's blood level. However, this can be wasteful to the overall blood supply, and perhaps more importantly, might unnecessarily expose the patient to infectious diseases. Moreover, an unnecessary transfusion could also result in less than optimal conditions for the patient, which can be particularly important during surgery. Thus, an apparatus for determining the amount of blood loss during a surgical operation or procedure is needed.

U.S. Pat. No. 4,773,423 to Hakky describes an arrangement for determining blood loss in which blood is collected by a vacuum tube, and is urged or squeezed from collected swabs or other material, and thereafter, the amount of blood loss is determined by the hemoglobin content. However, this arrangement has two significant problems. First, it is difficult to gather all of the blood lost by the patient by direct vacuum or by squeezing the blood from swabs or sponges utilized during surgery. Thus, in the Hakky arrangement, the amount of blood gathered does not reasonably approximate the entire amount of blood lost. In addition, the Hakky arrangement relies upon a direct color measurement of the reagent solution, and such a direct measurement can be quite inaccurate. For example, hemoglobin is generally a mixture of varying forms, each having different absorption spectrums. In addition, any fluid obtained from the patient will also include a variety of dissolved and solid impurities, and the turbidity of the sample can complicate direct colorimetric measurement. Thus, a direct color measurement of a solution will not provide a reliable indication of the amount of blood loss during surgery.

Accordingly, an apparatus which can accurately and rapidly provide a reliable indication of the amount of blood lost during a surgical operation or procedure is needed. Such an arrangement should be relatively easy to operate, and should provide a fairly immediate approximation of the amount of blood loss to inform the physician, and allow him or her to determine whether a blood transfusion is necessary.

SUMMARY OF THE INVENTION

Accordingly, it is an object of the present invention to provide a blood loss monitor which a physician can easily and effectively utilize to provide an accurate approximation of the amount of blood loss by a patient.

It is another object of the present invention to provide a system into which blood and blood containing materials may be deposited, with the system removing the blood from the materials and automatically analyzing a solution to provide a visual display of the amount of blood loss.

It is a further object of the present invention to provide a blood loss monitor which provides an immediate indication of the amount of blood loss, for example to provide an indication of the amount of blood loss within four or five minutes from the time blood and blood containing materials are deposited, and preferably in less time.

It is yet another object of the present invention to provide a blood loss monitor which can continuously and automatically monitor the amount of blood loss by a patient as surgery progresses, with the system providing a display which is periodically (typically short periods) updated as the surgery progresses.

These and other objects and advantages are attained in accordance with the present invention which provides a blood loss monitor which can continuously and progressively provide an indication to the physician as to the amount of blood loss by a patient during surgery without any substantial additional effort by the physician. In accordance with the present invention, a tank is provided which contains a suitable eluent solution which, as discussed in my earlier application (incorporated herein by reference), causes the blood to be released from the blood containing materials, such as sponges, pads or linen, even if the blood has dried somewhat in the materials. As the blood is released, an eluate solution is formed in the tank which includes the eluent and the blood lost by the patient, as well as other liquids which are deposited with the blood and blood containing materials (e.g., irrigating fluids utilized during surgery or other bodily fluids of the patient).

Significantly, the initial volume of the liquid in the tank is known (i.e., before the deposit of the blood and blood containing materials), and a volume indicating substance is also contained in the eluent solution, such that the initial concentration of the volume indicating substance is known. As the volume in the tank increases, the concentration of the volume indicating substance will correspondingly decrease. A volume indicating system can therefore readily determine the current volume of liquid in the tank simply by measuring the concentration of the volume indicating substance in the tank at a given time. The blood loss monitor in accordance with the present invention thus periodically or continuously obtains a sample from the tank which is analyzed to determine the concentration of the volume indicating substance to provide an indication of the liquid volume.

A sample is also utilized for determining the hemoglobin concentration contained in the sample. In particular, the amount of hemoglobin present in a sample from the tank at a given time is determined photometrically, thus yielding an indication of the present hemoglobin concentration in the tank. By utilizing the information relating to the current volume and the current hemoglobin concentration, the total amount of hemoglobin present in the tank is then calculated. Information relating to the hemoglobin amount together with the patient's known hemoglobin concentration (which is measured before surgery), allows for an accurate computation of the total volume amount of blood loss during the procedure up to the time of the sampling analysis. Information relating to the amount of blood loss and/or the amount of hemoglobin loss is then visually displayed to the physician.

BRIEF DESCRIPTION OF THE DRAWINGS

A more complete appreciation of the invention and many of the attendant advantages thereof will be readily apparent from the following detailed description, particularly when read in conjunction with the drawings in which.

DETAILED DESCRIPTION OF THE PREFERRED EMBODIMENT

Figure 1:
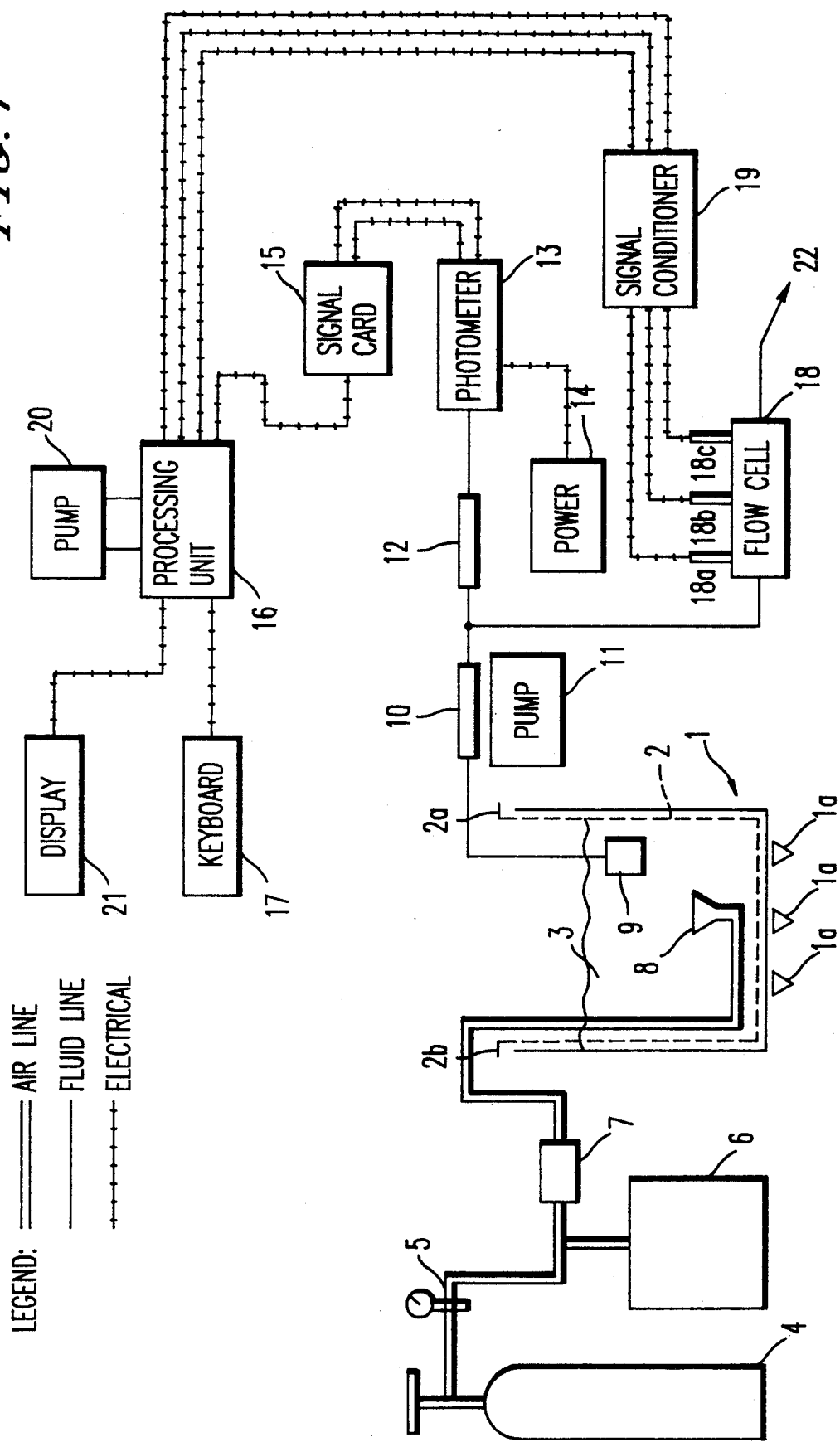
FIG. 1 is a schematic diagram of the blood loss monitor of the present invention.

Referring now to FIG. 1, a schematic of the blood loss monitor of the present invention is shown. For illustrative purposes, in FIG. 1 the double lines indicate gaseous fluid lines, the single lines indicate liquid passages or tubing, with the crossed single lines representing electrical connections. The system includes a tank 1 which contains a suitable eluent solution 3 as discussed in my earlier application. The eluent solution is sufficient to allow blood to be removed from the blood containing materials, and also to allow for hemolysis, or the liberation of hemoglobin from the blood. Preferably, the tank allows for a liquid volume level on the order of 10 gallons, so that suitable proportions of the eluent and blood are present which can be readily analyzed. Of course, larger or smaller tanks could also be utilized where appropriate. Moreover, the tank should have sufficient dimensions so that the blood containing materials can be readily agitated to assist removal of the blood from the materials. In addition, the tank preferably includes ultrasonic transducers 1a to agitate the liquid in the tank thereby assisting mixing and disassociation of the blood from the blood containing materials.

A gaseous fluid agitation system may also be provided to further assist in the removal of the blood from the blood containing materials and to prevent the materials from clumping together. This system can include for example a source of nitrogen gas 4 which is regulated by a pressure regulator 5, and held in reservoir tank 6, from which a solenoid valve 7 then provides the gaseous fluid to flow to the tank intermittently via diffuser 8, such that the materials in the tank are sufficiently agitated by the gas as it bubbles through the liquid contained in the tank. Although both gaseous and sonic agitation are shown in FIG. 1, currently it is believed that both should not be used together or at least not simultaneously, since the ultrasonic vibrations will simply tend to remove gas from the liquid prior to being effective in assisting removal of blood from the blood containing materials. If desired, mechanical agitation could be used in lieu of or in addition to the bubbling or ultrasonic agitation.

Preferably, the tank 1 also includes a basket 2 which is supported so as to lie inside the tank and ensures a spacing between the blood containing materials and the walls of the tank. This can ensure effective agitation of the blood containing materials, since they are prevented from accumulating in remote portions or corners of the tank. Perhaps more importantly, the basket 2 will also ensure that the blood containing materials will not interfere with the operation of the ultrasonic transducers. The basket can be supported, for example, by a brim 2a which supports the basket on the outer periphery of the tank. If desired, the basket can also be provided with a handle 2b, such that the basket can be readily removed, simultaneously removing the materials which have previously been deposited into the tank such as sponges, instruments etc. Of course, the basket would require the provision of apertures to accommodate the diffuser or other agitation means, preferably with the apertures sized so that blood containing materials will not pass between the periphery of the aperture and any agitating device.

Thus, the tank 1 includes an eluent 3, with the tank being agitated by ultrasonic vibrations and/or mechanical agitation and/or bubbling action of the gaseous fluid. During surgery, blood containing materials, such as sponges, pads, linens, instruments etc., as well as blood from suction devices, are deposited into the tank. The blood is mixed with the eluent solution, and the eluent solution causes removal of blood from the blood containing materials as well as lysis of the hemoglobin-containing red blood cells, such that the entire amount of hemoglobin from the blood and blood containing materials is substantially uniformly mixed in the tank solution.

A baffle and filter arrangement 9 is provided to remove a sample from the tank, without removing any particulate matter, so that the liquid in the tank can be analyzed. The sample is removed by a pump tube manifold 10 and peristaltic pump 11, which draws a sample from the tank and provides the sample to: (1) a flow cell 18 which is utilized to determine the total volume of liquid in the tank; and (2) a processing/switching module 12 which will provide processed samples to be analyzed for hemoglobin content.

As discussed earlier, prior to surgery, the eluent in the tank contains a volume indicating substance of a known concentration, and the initial volume of the liquid in the tank is also known. As blood and other liquids are deposited into the tank, the concentration of the volume indicating substance is correspondingly decreased, such that by determining the concentration of the volume indicating substance, the total volume of liquid in the tank can be determined. For example, where the initial volume of the tank is 10 gallons, and after depositing liquids into the tank, the concentration of the volume-indicating substance has dropped to two-thirds of the initial concentration, it is known that the volume of liquid in the tank has increased to three-halves of that of the initial volume, or in other words 15 gallons of liquid is no present in the tank. It is extremely important to maintain an accurate measure of the liquid in the tank to make the hemoglobin concentration measurements (discussed hereinafter) meaningful. As blood is introduced into the tank, irrigating fluids and other liquids are also deposited, such that changes in hemoglobin concentration alone are insufficient to determine the total blood loss.

In accordance with the present invention, the volume-indicating substance is an ion, such as lithium or fluoride. The eluate sample from the tank provided to flow cell 18 is then analyzed for the concentration of the ion, by utilizing ion-sensitive electrodes. For example, where lithium is utilized, electrodes 18a–c are provided to determine the concentration of lithium in the solution at a given time. One of the electrodes will provide an indication of the amount of lithium present by comparison with a reference signal 18c. An additional electrode 18b, which is sensitive to sodium, may be utilized for a sodium correction, since extraneous sodium ions (often present in blood or irrigating fluids) may also be measured by the lithium electrode 18a. Other means may be provided to correct for the presence of sodium ions which can have an effect of only about 1% on the determination of the lithium concentration.

Although lithium may be utilized as the volume indicating substance, it has been determined that the use of fluoride is more adaptable to measurement utilizing ion sensitive electrodes. Fluoride sensitive electrodes are more readily available, and are not affected by the presence of sodium. Accordingly, for fluoride, a single combination electrode may be utilized to provide both a fluoride signal and a reference signal. In addition, lithium cannot be utilized where the patient has undergone lithium therapy.

The ion-sensitive electrodes 18 thus provide voltage signals to a signal conditioner 19, which in turn provides signals to a computer or processing unit 16 having a data acquisition module. The computer will thus receive the information, and by the differences in the signals (i.e, the ion sensitive electrode and the reference electrode), the concentration of the volume-indicating substance is determined, from which the total volume of liquid present in the tank 1 is calculated. After the volume analysis, the sample can be returned to tank 1 as indicated at 22.

The analysis of the hemoglobin content in the blood involves a dual-channel photometer or a dual-time photometer represented at 13. With a dual channel arrangement, the sample is divided into two samples which are separately analyzed, with the difference in signals determining the hemoglobin level in the sample. With the dual time photometer arrangement, the same sample is utilized with the photometric readings taken sequentially (with an additional substance added between taking of each signal), again with the difference in signals indicating the hemoglobin level.

More particularly, the hemoglobin level determining system includes a processing/switching module 12. Here, two samples (or subsamples) are provided, one of which is to be analyzed for the presence of methemoglobin, the other of which is to be analyzed for the presence of cyanmethemoglobin. The samples can either be provided by separate conduits which are connected to the photometer 13, or alternatively, the samples may be sequentially prepared from a single sample drawn from the tank, with the samples analyzed one after the other by the photometer 13. In any case, the processing/switching module 12 and photometer 13 are utilized to photometrically analyze two samples from a sample of eluate drawn from the tank, with the photometer suitably powered by a power supply 14.

As discussed in my earlier application, one of the samples includes a buffer, potassium ferricyanide and water. This converts all of the hemoglobin present in the sample to methemoglobin. The other sample includes the buffer and potassium ferricyanide, however with cyanide also added instead of water. Water is added to the first sample, merely to provide a volume substitute for the cyanide of the second sample, so that equal proportions of the eluate are present in each sample. The cyanide and potassium ferricyanide added to the second sample converts all hemoglobin to cyanmethemoglobin. Photometry of the first sample at 632 nm will yield the absorbances of all extraneous matter as well as methemoglobin. Since the absorbance of cyanmethemoglobin at 632 nm is not significant, photometry of the second sample will mainly yield the absorbance of all extraneous matter. Thus, the difference in the absorbances is proportional to the concentration of hemoglobin in the eluate. Alternatively, photometry of both samples at 540 nm will give a similar differential, since cyanmethemoglobin will absorb at 540 nm but, methemoglobin will not to the same extent, and the concentration of hemoglobin can thus be obtained.

It is extremely important to utilize dual photometric readings to account for extraneous matter. Extraneous matter can result from small particles of the blood containing materials, or possibly from surfaces from which blood has been retrieved in the operating room. For example, if during surgery blood falls to the floor, even this blood can be measured by wiping the blood from the floor and tossing the linen into the tank.

It is also possible for the first and second samples to be sequentially provided and examined, with the first sample including the eluate, buffer and potassium ferricyanide analyzed, and thereafter adding cyanide to the sample to produce the second sample which is then analyzed. However, in this arrangement, the change in the proportion of the eluate to the sample must be accommodated in the determination, and thus it is preferable to utilize two separate photometric test samples from the sample drawn from the tank 1.

The dual channel photometer 13 thus takes two photometric measurements and produces signals indicative thereof which are provided to a signal conditioner 15. The signal conditioner provides the difference of these signals to the computer 16 such that the hemoglobin concentration in the eluate is determined. The use of signal conditioners is particularly necessary since the voltages vary logarithmically with the concentration, and thus must be converted to vary linearly to allow for comparison of the signals.

Thus, from the hemoglobin concentration determining system and the volume indicator concentration determining systems, the computer 16 can acquire all of the information necessary to determine the total amount of hemoglobin and blood loss. In particular, the current volume of liquid in the tank is calculated by multiplying the initial volume of liquid in the tank by the ratio of the initial concentration of the volume indicating substance to the current concentration of the volume indicating substance as determined at the flow cell 18 (i.e., the current volume is the product of the initial volume times the initial concentration divided by the current concentration). The current amount of hemoglobin (in grams) in the tank 1 is then determined utilizing the hemoglobin concentration (in g/L) from the hemoglobin concentration determining system, and multiplying this by the total volume in the tank calculated as discussed above. Next, the blood loss is determined by multiplying the hemoglobin amount (in grams) by 100, and dividing by the patient's hemoglobin concentration (g/dL), which has been measured immediately prior to the surgery, and may be input, for example by a keyboard unit 17. A CRT display 20 is also provided to give an immediate display of the results to the physician. An additional display 21 may be also be provided so that the display can be readily seen at more than one location inside or outside of the operating room.

It could also be possible to provide a direct measure of the patient's hemoglobin level or concentration to the computer, for example by providing a system which can photometrically analyze a sample of the patient's blood at periodic intervals. With the direct measurement, the presurgery measurement need not be relied upon. In addition, it should be noted that it could also be desirable to display the total amount of hemoglobin loss in grams, since this could become important in monitoring/controlling the patient's vital signs during surgery. For example, it may be desirable to maintain the hemoglobin level somewhat below normal during surgery to reduce the amount of work required by the heart, and a measure of the total mass of hemoglobin lost would therefore be helpful. Information regarding the mass of hemoglobin loss may even be more useful in allowing a physician to control a patient's condition, and since the computation of total hemoglobin lost does not require a measure of the patient's initial hemoglobin level, it is not subject to error should the patient's hemoglobin level change during surgery.

Thus, in accordance with the present invention, blood and blood containing materials are deposited into an ultrasonic tank, with samples periodically analyzed to determine both the hemoglobin concentration of the sample as well as the concentration of a volume indicating substance. From this information, as well as the initial information relating to: (1) the patient's hemoglobin level; (2) the initial concentration of the volume indicating substance, and (3) the initial volume of the liquid in the tank, the amount of blood loss can be determined. Each succeeding measurement or analysis of the samples provides progressively updated information as to the total amount of blood loss during surgery.

Figure 2:
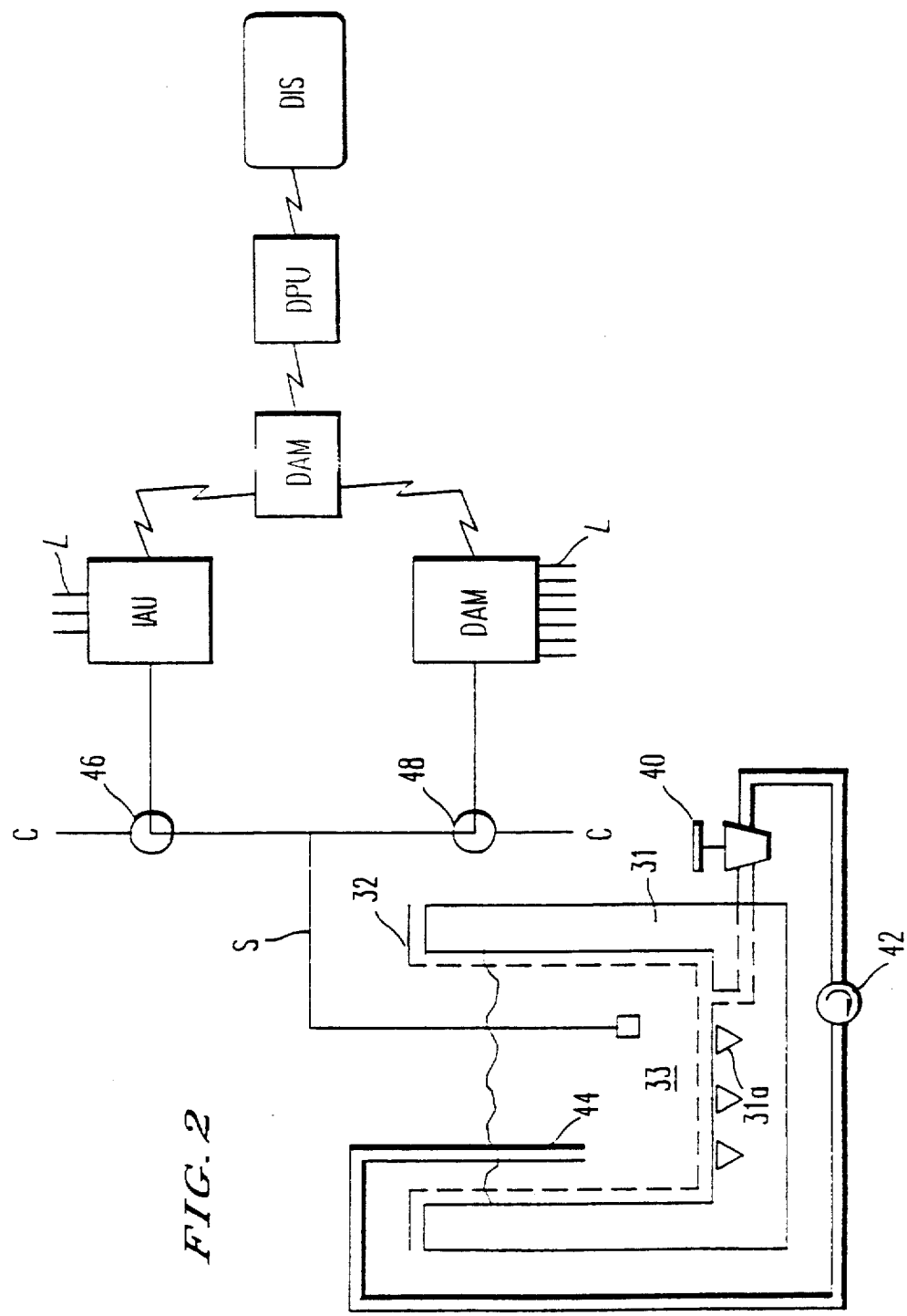
FIG. 2 is a modified embodiment of the present invention.
Figure 3:
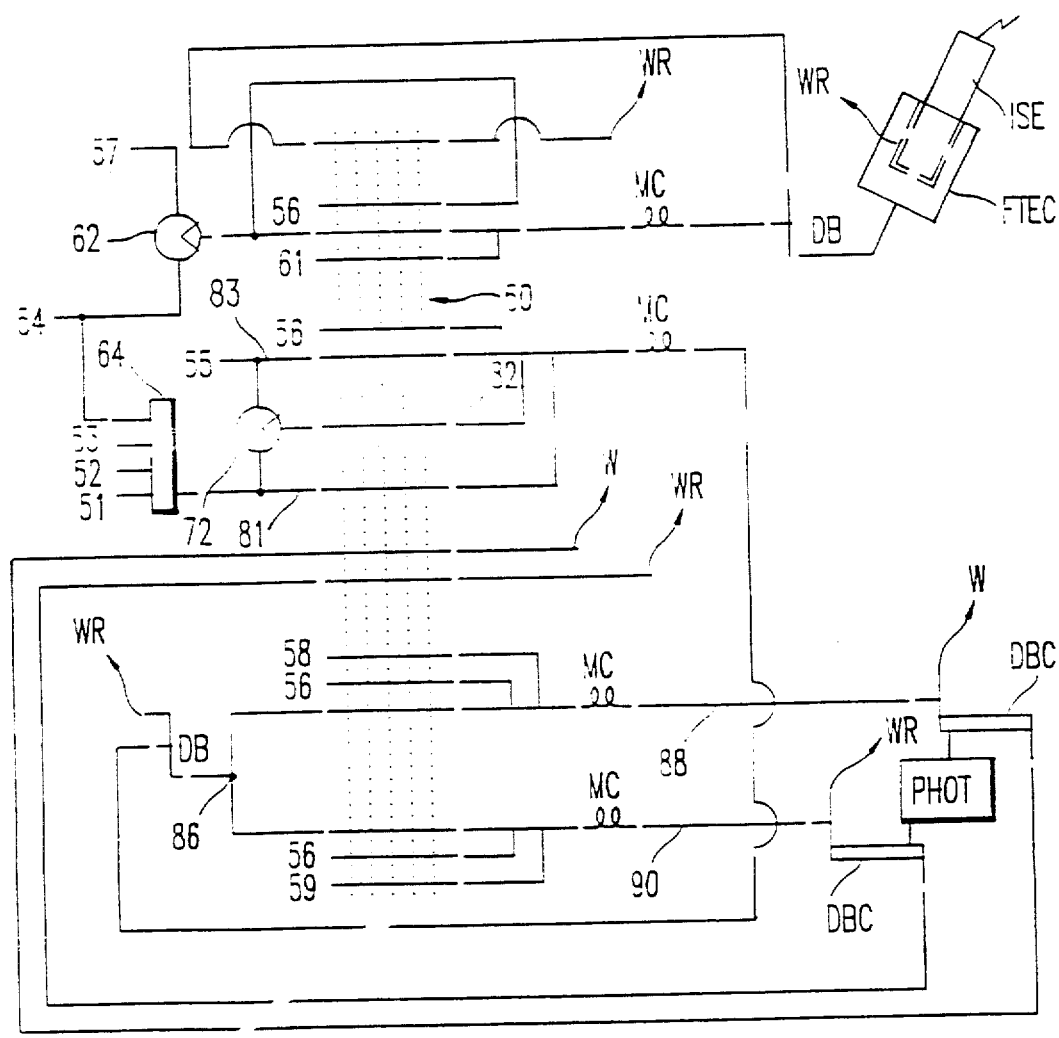
Figure 4:
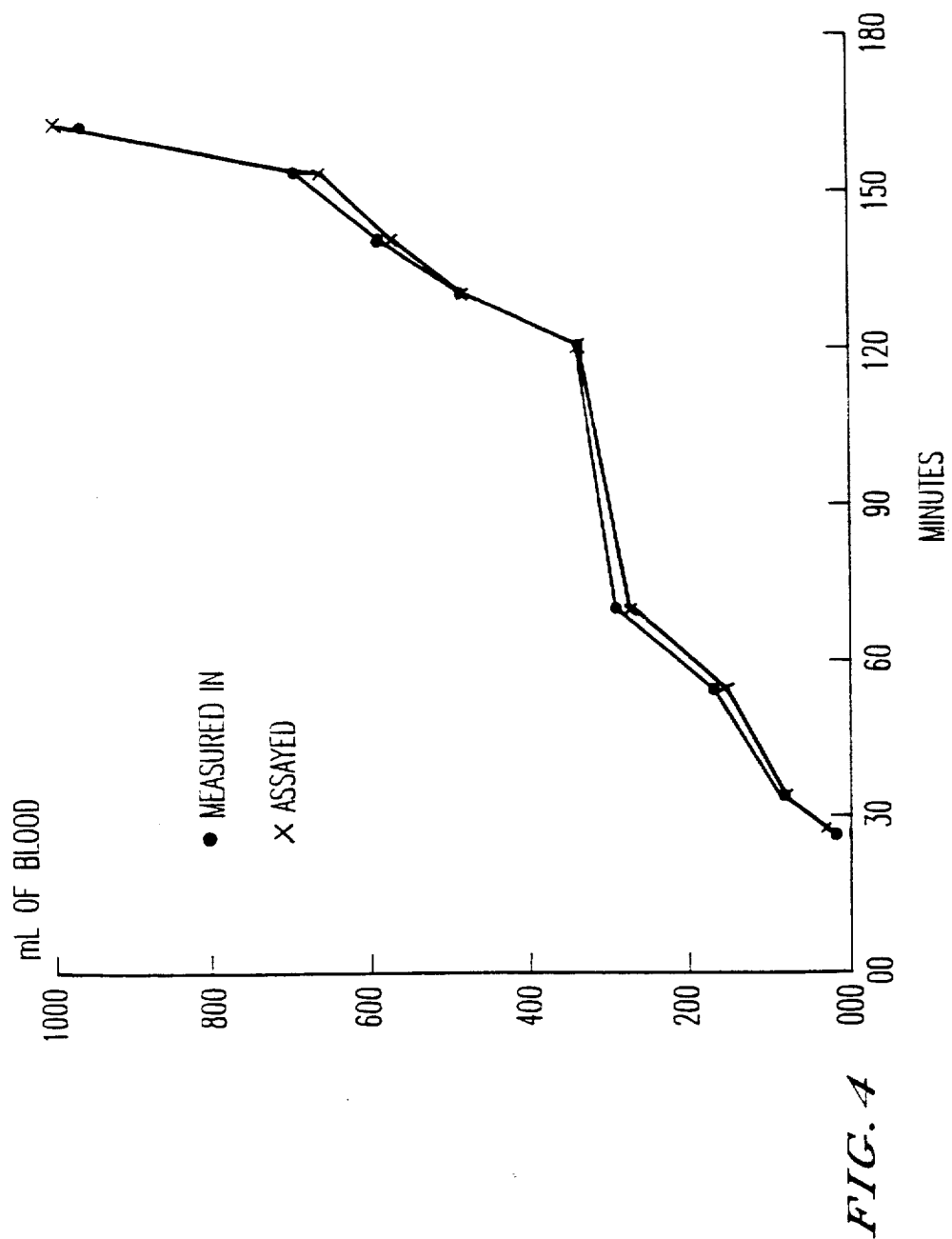
Figure 2:
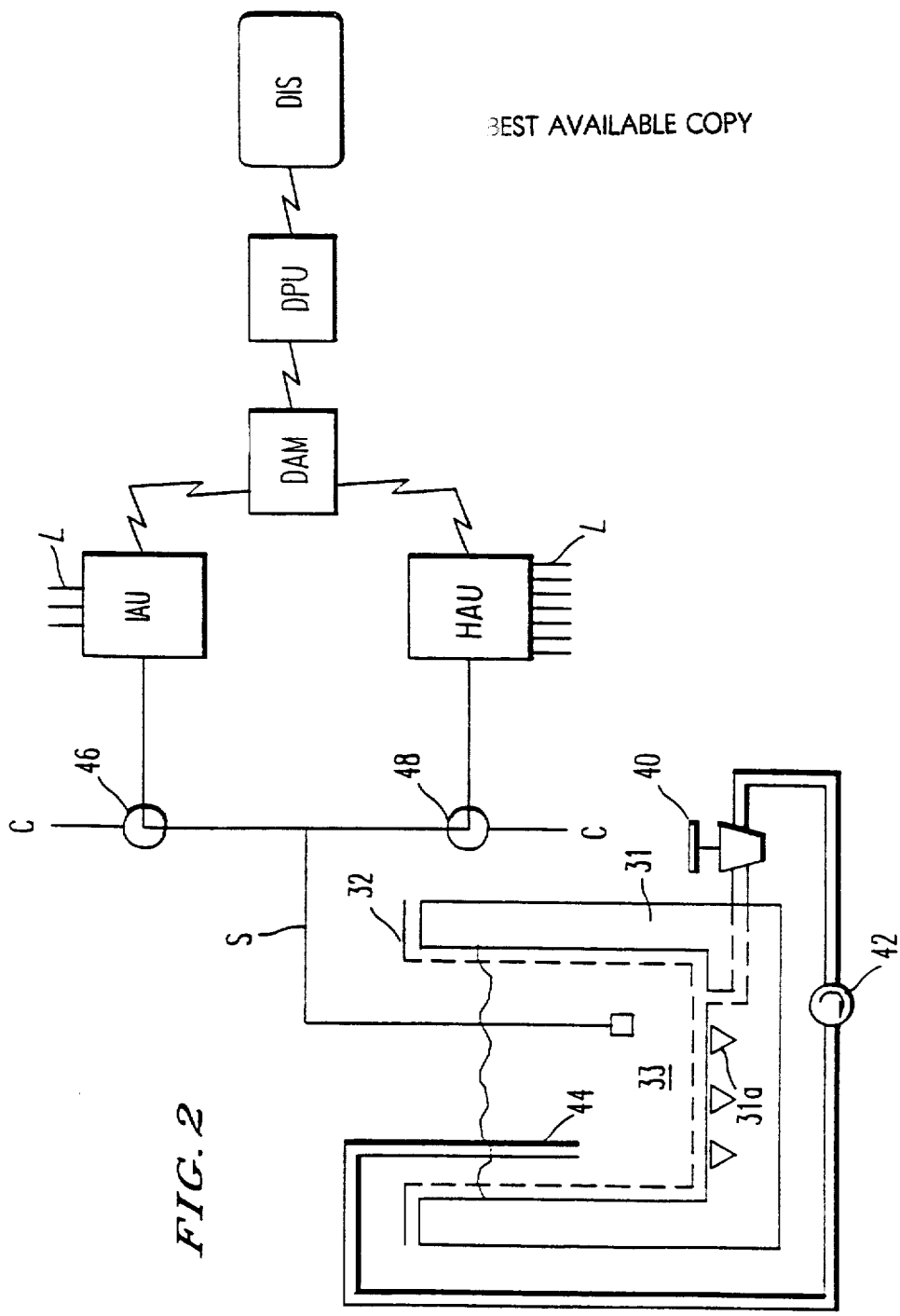

Referring now to FIG. 2, a modified version of the present invention is shown in a simplified schematic diagram. In FIG. 2, a hollow walled tank 31 is provided having the eluent solution 33 and basket 32 disposed therein. Ultrasonic transducers 31a are also provided to assist in removal of the blood from the blood containing materials. In addition, a circulating system is provided which includes a valve 40 and pump 42 which removes liquid from the lower end of the tank and redeposits the liquid as shown at outlet 44, thereby promoting movement of the fluid in the tank and mixing of the liquids.

The recirculation system is also conveniently utilized to remove the liquids from the tank after completion of surgery, simply by relocating the outlet 44 to communicate with a drain or other suitable waste deposit location. As in the earlier embodiment, a sample is drawn from the tank 31 along sampling line S. Samples or subsamples are delivered to the hemoglobin analyzing unit (HAU) and the ion-analyzing unit (IAU) via respective valves 48, 46. The valves allow for respective control samples or calibrator samples to be delivered from respective sources as indicated at C, with the samples delivered to the analyzing units prior to analyzing any of the eluate samples. The calibrator samples delivered at C include respective hemoglobin samples and ion samples of known concentrations, thereby allowing the voltage meters and/or displayed signals to be calibrated based upon known ion and hemoglobin concentrations. To ensure accurate analysis of the samples, calibration of the hemoglobin analyzing and ion analyzing systems should be performed prior to each use. After calibration, the valves 48, 46 are turned to the positions indicated in FIG. 2, such that the samples are provided to the HAU and IAU, with the additional inlet/outlet lines L provided for the additional reagents to be added as well as allowing for exit of waste from the analyzing units. The information obtained from the ion-analyzing unit and hemoglobin-analyzing unit are then transmitted to the data acquisition module (DAM), which in turn provides information to the digital processing unit (DPU), and finally the information is displayed at the display (DIS) in the form of the total amount of blood loss and/or the total amount of hemoglobin loss.

Figure 3:
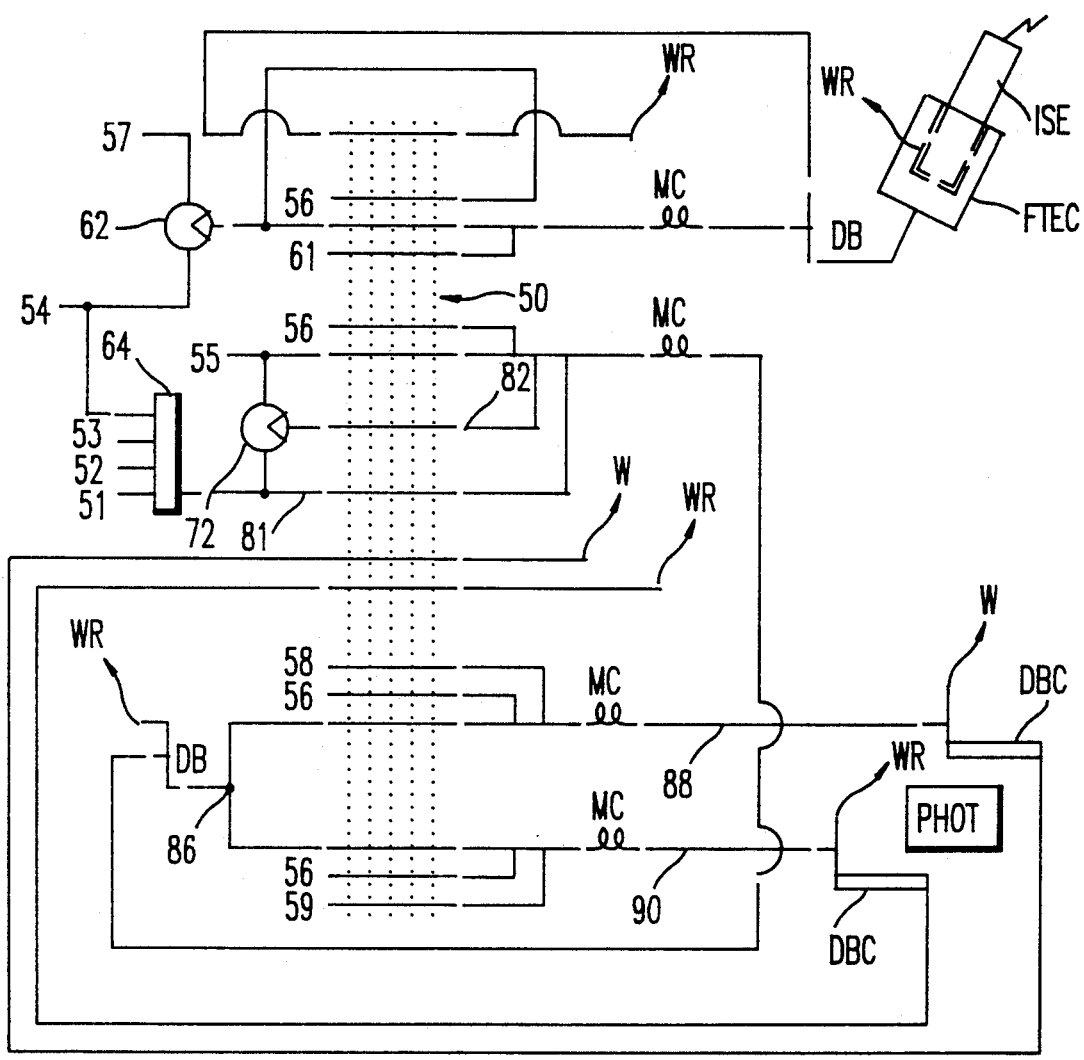
FIG. 3 is a flow diagram indicating the flow of various fluids in the blood loss monitor for determining the various properties of an eluate sample to provide an indication of the total amount of blood lost.

Referring now to FIG. 3, a description of the handling of the eluate sample and the various reagents for analysis is described. For clarity, like numerals are utilized to designate inlets for like materials or reagents, however, it is to be understood that a single common source may be provided for each of the inlets for a given reagent, or alternatively, a separate supply, such as a bottle of a given reagent, may be utilized for each inlet. In FIG. 3, the dotted or shaded section 50 indicates pump tubes where the pumping direction is left to right in the passages covered by the shaded region 50. As a result of the pumping action, a sample of eluate is drawn into the system as indicated at 54. As discussed earlier, prior to analysis of the sample, with valve 62 in a first position, the ion-analyzing unit can be provided with a control material or calibrator 57 utilized for calibrating the ion sensitive electrode (ISE), with the two-way valve 62 provided for delivering the ISE calibrator material rather than the eluate sample. After calibration, the two-way valve 62 is switched to deliver the sample 54 rather than the calibrator material.

A four-way valve is also provided as shown at 64 (which corresponds to the valve 48 in the simplified schematic of FIG. 2) to selectively provide either the sample or calibrating materials to the hemoglobin analyzing system. However, for calibration of the hemoglobin analyzing unit, two control samples or calibrators 52, 53 are preferably utilized. In particular, a low hemoglobin calibrator 52 is provided to yield a calibration reference point for low hemoglobin concentrations. In addition, a high hemoglobin calibrator 53 is provided for a reference calibration value for high hemoglobin levels. The use of high and low hemoglobin calibrators allows for greater flexibility in the system, and ensures more accurate measurement for both low hemoglobin concentrations (e.g. during the initial stages of the operation where the amount of blood in the tank 1, 31 is low)

and for high hemoglobin concentrations (e.g. after a great deal of blood has been lost and deposited into the tank as the operation progresses). Thus, prior to analyzing the sample, the hemoglobin analyzing system is calibrated by successively using the low and high calibrators 52, 53. Subsequently, the four-way valve 64 is switched to allow for analysis of the sample from 54. A buffer can also be added at the four-way valve as indicated at 51, for reference purposes.

Referring to the upper portion of the FIG. 3, the ion-analyzing system is shown. After calibration, a sample is drawn from 62, and is mixed with air from source 56 and a buffer from source 61 which, as indicated in the drawing, are pumped to be combined with the sample. The air is provided to improve the flow characteristics as well as the mixing of the materials. The fluids pass through a mixing coil MC and then through a debubbler DB which removes air so that it does not affect the ion analysis for determining the total volume in the tank (1,31). The sample then passes to a flow through electrode cell (FTEC) at which an ion sensitive electrode (ISE) produces a signal which corresponds to the concentration of the ion material in the solution. As discussed earlier, the ion sensitive electrode may take the form of a combination electrode which, for example, can include a fluoride sensitive electrode and a reference electrode for sensing the concentration of fluoride in the sample. After the ion analysis is completed, the sample may be disposed to waste or recovered to tank 1, as can be any excess of the sample which is not required for use in the analysis. All samples drawn and/or processed not containing cyanide are preferably recovered from waste (indicated as WR) and returned to tank 1. Samples containing cyanide are removed as waste (W).

In analyzing the hemoglobin concentration, after calibration of the hemoglobin analyzing unit, the four way valve 64 delivers the sample 54 to be mixed with ferricyanide 55 and air 56. Significantly, an additional two-way valve is provided as shown at 72. It has been recognized that photometric analysis tends to be more accurate for certain concentrations of hemoglobin. Thus, for situations in which the surgery has just begun, where the blood loss is low, it is desirable to utilize a greater proportion of the eluate sample in the analysis. Thus, for low amounts of blood loss, the valve 72 is in a first position such that two lines containing the liquid from valve 64 are provided through lines 81, 82. By contrast, where the blood loss is high, the valve 72 is shifted to a second position such sample passes only through line 81, while the ferricyanide is allowed to pass through both lines 82 and 83, such that the proportion of the eluate in the liquid to be analyzed is reduced. By varying the proportions of the eluate sample utilized in the analysis, the sensitivity of the analysis can be retained for both low and high levels of blood loss. The use of the low and high hemoglobin calibrators may also be coordinated with the positioning of the valve 72, for example with the low hemoglobin calibrator utilized when the valve is in the first position (i.e., communicating the flow from valve 64 to both lines 81 and 82), and with the valve 72 in the second position for the high hemoglobin calibrator (i.e., such that the flow from 64 communicates only with line 81).

Air is also added to the liquid as shown at 56, again to promote proper flow characteristics as well as to promote mixing of the liquids. The air, together with the liquids from lines 81-83 are then combined and pass through a mixing coil MC, and the liquid thus obtained is divided into two channels as shown at 86 for photometric analysis. Prior to division of the sample at 86, an additional debubbling device DB may be provided to eliminate excess air from the liquid. In addition, excess liquid may also be removed as indicated at WR.

As discussed above, the hemoglobin concentration analysis includes two parts, one in which cyanmethemoglobin is present and the other of which methemoglobin is present. Thus, for a first portion of the sample or subsample, water 59 and air 56 are added to the liquid flowing from junction 86. The subsample is mixed as shown at MC, and then passes to a debubbling cuvette (DBC). In the second subsample, cyanide 58 and air 56 are combined with the liquid flowing from the junction 86, with the mixture passing through the mixing coil MC and the debubbling cuvette (DBC). The dual-channel photometer (PHOT) then performs the photometric analysis, with the hemoglobin concentration thus determined based upon differences int he absorbances of the liquids supplied respectively from tubes 88 and 90. Although the byproducts may be discarded as indicated at W, in the use, only the cyanide containing materials (i.e., which have passed through line 88) must be discarded, whereas the remaining excess materials (WR) may simply be returned to the tank. Thus, as shown in FIG. 3, the eluate sample is analyzed for hemoglobin concentration as well as for the concentration of the ion or volume indicating substance so that information regarding the amount of hemoglobin and blood loss can be obtained.

Figure 4:
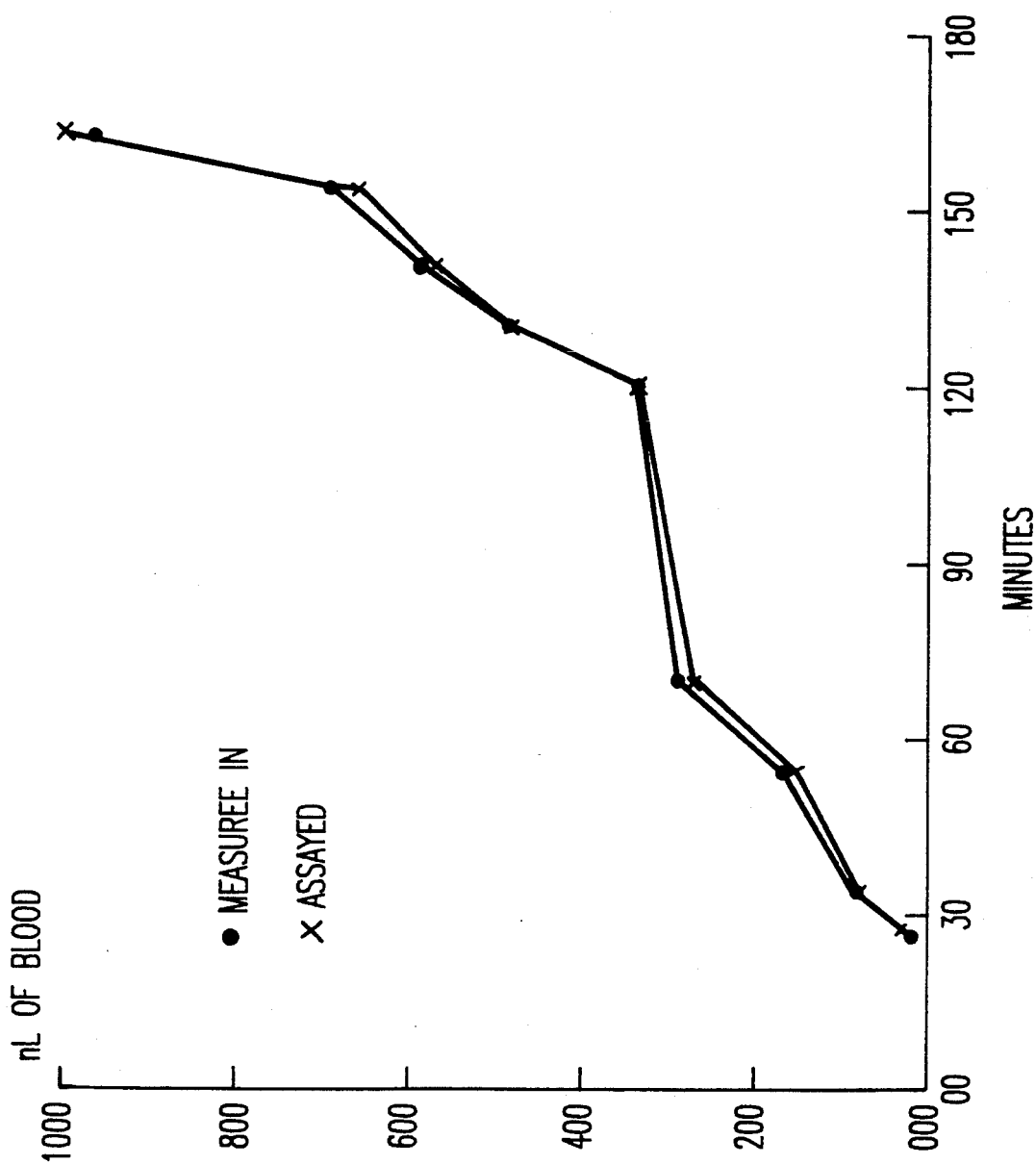
FIG. 4 is a graph of test data comparing actual and measured amounts of blood.

FIG. 4 plots data utilized in a test run of the apparatus as shown in FIG. 2, in which bovine blood was gradually added to the tank containing approximately 20 liters of an eluant. As is clearly demonstrated in FIG. 4, the assayed or automatically determined amount of blood loss of the blood loss monitor corresponds extremely well with the amounts measured into the tank, both from a standpoint of total loss of blood as well as the timing of the loss. Thus, in accordance with the present invention, the amount of blood loss during a surgical operation or procedure can be accurately tracked such that the physician can determine if and when a transfusion is necessary. In addition, as the ability to control body functions during surgery are refined, the measurement of total hemoglobin loss may also be utilized to assist such control.

In order to make the system effective and to provide confidence to the operating room personnel, a method or system should also be incorporated for keeping track of the materials which are deposited into the tank. This is particularly important, since the operating room personnel must ensure that various objects are not left in the patient upon completion of the surgery. Thus, either a manual counting system or an automatic counting system should be utilized for maintaining a count of the articles deposited into the tank to ensure that no articles are left in the patient. This will avoid the necessity of collecting and counting the articles after they are deposited into the tank which would not only be messy and unsanitary, but also could effect the accuracy of the analysis due to removal of liquids with the materials as they are removed form the tank.

Obviously, numerous modifications and variations of the present invention are possible without departing form the spirit of the present invention in light of the above teachings. It is therefore to be understood that within the scope of the appended claims, the invention may be practiced otherwise than as specifically described herein.

What is claimed as new and desired to be secured by Letters Patent of the United States is:

1. An apparatus for obtaining an approximation of blood loss in a patient during a surgical procedure comprising:
   a tank into which blood carrying materials generated during said surgical procedure are deposited, said tank including an eluent;
   a volume determining system in fluid communication with said tank providing a measure of volume of liquid in said tank;
   a hemoglobin concentration determining system in fluid communication with said tank for determining hemoglobin concentration in said tank; and
   a processing unit electronically connected to said volume determining system and said hemoglobin concentration determining system programmed for calculating the amount of blood loss experienced by said patient during said surgical procedure based upon the hemoglobin concentration, the volume of liquid in said tank, and the patient's hemoglobin level measured immediately prior to surgery.

2. The apparatus of claim 1, wherein said volume determining system and said hemoglobin concentration determining system are each capable of providing periodic signals to said processing unit relating to volume of liquid int eh tank and hemoglobin concentration in the tank, to thereby provide updated information relating to the volume of liquid in the tank and the hemoglobin concentration in the tank, and wherein the processing unit periodically updates the calculation of the amount of blood loss such that the amount of blood lost during a surgical procedure can be monitored as surgery progresses.

3. The apparatus of claim 2, wherein the tank includes a volume indicating material of a known initial concentration, and wherein said volume determining system includes means for determining an updated value of concentration of the volume indicating material such that the updated volume of liquid in the tank can be calculated based upon the initial volume, the initial volume indicating material concentration and an updated volume indicating material concentration.

4. The apparatus of claim 3, wherein the volume indicating material is an ion, and said volume determining system includes an ion-sensitive electrode.

5. The apparatus of claim 2, wherein said hemoglobin concentration determining system includes optical analyzing means for determining the hemoglobin concentration optically.

6. The apparatus of claim 5, wherein said hemoglobin concentration determining system includes a conduit for receiving an eluate sample from said tank and preparing two subsamples, one of which includes methemoglobin, and the other of which includes cyanmethemoglobin, and wherein the concentration of hemoglobin in said tank is determined based on the difference in absorbances of methemoglobin and cyanmethemoglobin, as determined by the amount of light passing through said sub-samples, said light being provided from a light source at a wavelength of either 632 nm or 540 nm, said transmitted light being measured by a photometer situated opposite said light source from said sub-samples.

7. The apparatus of claim 1, wherein said tank further includes means to agitate liquids and blood containing materials contained in said tank.

8. The apparatus of claim 6, wherein said means to agitate liquids and blood containing materials comprises an ultrasonic transducer to sonically agitate the tank.

9. The apparatus of claim 2, wherein said tank further comprises means to agitate the tank includes a system for intermittent deliveries of a volume of gas to the tank to thereby agitate materials in the tank by a bubbling action.

10. The apparatus of claim 2, further including a display in electronic communication with said processing unit which provides a periodically updated display of the total blood loss.

11. The apparatus of claim 2, wherein said hemoglobin concentration determining system includes means for combining an eluate sample from the tank with a buffer and ferricyanide to form methemoglobin, and wherein a flow system is provided to divide a liquid thus obtained into first and second sub-samples, wherein means are also provided to introduce cyanide into one of the sub-samples to form cyanmethemoglobin, and wherein a photometer is provided for determining differences in absorbance properties between the first and second sub-samples relating to different absorbance properties of methemoglobin and cyanmethemoglobin to thereby determine the amount of hemoglobin int eh eluate sample.

12. The apparatus of claim 11, further including a valve in said fluid communication between said tank and said hemoglobin concentration determining system for varying the proportion of eluate samples in the sub-samples which are photometrically analyzed, such that for eluate samples having low hemoglobin concentrations, the proportion of eluate int he subsample analyzed is greater as compared with eluate samples having high hemoglobin levels in which the proportion of eluate int he analyzed subsamples is reduced.

13. The apparatus of claim 3, further including a recirculation system in said fluid communication between said tank and said hemoglobin concentration determining system for removing liquid from the tank at a first location, and for returning liquid to the tank at a second location.

14. The apparatus of claim 1, wherein the volume determining system includes an ion sensitive electrode for determining the concentration of an ion present in liquids contained in said tank.

15. The apparatus of claim 10, wherein said display is capable of providing a periodically updated display of hemoglobin loss in terms of mass units.

16. An apparatus for determining an amount of blood loss in a patient during a surgical procedure, comprising:
   a tank into which blood and blood containing materials generated during said surgical procedure are deposited, said tank including an eluent and a volume indicating substance;
   a volume determining system in fluid communication with said tank for providing an updated measure of volume of liquid in said tank by determining a concentration of the volume indicating substance; and
   a hemoglobin concentration determining system in fluid communication with said tank for determining hemoglobin concentration of liquid in said tank on an updated basis, said hemoglobin concentration determining system including means for preparing at least two sub-samples from an eluate sample withdrawn from said tank, wherein one of said sub-samples includes cyanmethemoglobin and the other of said sub-samples includes methemoglobin, said hemoglobin concentration determining system further including a photometer for measuring absorbances of the two sub-samples so such that the concentration of hemoglobin can be determined based upon differences in the absorbance characteristics of methemoglobin and cyanmethemoglobin, wherein the amount of blood loss is calculated based upon the determined hemoglobin concentration of liquid in said tank, the determined volume of liquid in said tank, and the patient's hemoglobin level measured immediately prior to said surgery.

17. The apparatus of claim 16, wherein both the sub-sample containing methemoglobin and the subsample containing cyanmethemoglin are analyzed at 540 nm or 632 nm such that the difference in the absorbance characteristics substantially corresponds to hemoglobin concentration in the eluate sample.

18. The apparatus of claim 16, wherein the sub-sample containing methemoglobin is analyzed at 540 nm to determine the presence of any extraneous matter, and wherein the subsample containing cyanmethemoglobin is analyzed at 540 nm to determine the presence of cyanmethemoglobin and any extraneous matter such that differences in absorbance signals corresponds to hemoglobin concentration in the eluate sample.

19. The apparatus of claim 16, wherein said hemoglobin concentration determining system further comprises a reagent supply means for adding reagents to the eluate sample and sub-samples so as to form said methemoglobin and said cyanmethemoglobin.

20. The apparatus of claim 16, wherein said hemoglobin concentration determining system further comprises a hemoglobin calibrator supply system for providing a known liquid to the hemoglobin concentration determining system, and said volume determining system further comprises a volume calibrator supply means for supplying a known liquid to the volume of liquid in said tank, such that said hemoglobin concentration determining and said volume determining systems can be calibrated.

* * * * *

UNITED STATES PATENT AND TRADEMARK OFFICE
CERTIFICATE OF CORRECTION

PATENT NO. : 5,236,664
DATED : August 17, 1993
INVENTOR(S) : LUDVIGSEN

It is certified that error appears in the above-indentified patent and that said Letters Patent is hereby corrected as shown below:

Title page should be deleted and replaced with the attached Title page.

In column 1,
   line 67: "spectrums" should read --spectra--
   line 68: "will" should read --may--

In column 2,
   line 19: "blood loss" should read --blood lost--
   line 44: "loss by" should read --loss from--

In column 5,
   line 8: "no" should read --now--
   line 29-32: "sodium ions which can have an effect of only about 1%" should read --sodium ions from which an effect of only about 1% on the lithium concentration is allowable--

UNITED STATES PATENT AND TRADEMARK OFFICE
CERTIFICATE OF CORRECTION

PATENT NO. : 5,236,664
DATED : AUGUST 17, 1993
INVENTOR(S) : LUDVIGSEN

It is certified that error appears in the above-identified patent and that said Letters Patent is hereby corrected as shown below:

In column 8, line 9:
    "the samples" should read --the calibrator samples--

In column 9, line 49:
    "such" should read --so that--

In column 10,
    line 19: "int he" should read --in the--
    line 61: "effect" should read --affect--

In column 11,
    line 23: "patient 's" should read --patient's--
    line 31: "int eh" should read --in the--

In column 12,
    line 4, claim 8: "The aparatus of claim 6" should read --the apparatus of claim 2 or 7--
    line 28, claim 11: "int eh" should read --in the--
    line 36, claim 12: "int eh" should read --in the--
    line 39, claim 12: "int he" should read --in the--

In column 13, line 8, claim 16:
    "so such that" should read --so that--

UNITED STATES PATENT AND TRADEMARK OFFICE
CERTIFICATE OF CORRECTION

PATENT NO. : 5,236,664
DATED : August 17, 1993
INVENTOR(S) : LUDVIGSEN

It is certified that error appears in the above-indentified patent and that said Letters Patent is hereby corrected as shown below:

Please replace Figures 1, 2, 3, and 4 with enclosed corrected Figures 1, 2, 3 and 4.

Please repace the drawing on the Abstract page with enclosed corrected Figure 1.

Signed and Sealed this

Second Day of May, 1995

Attest:

BRUCE LEHMAN

*Attesting Officer*   *Commissioner of Patents and Trademarks*

United States Patent [19]

Ludvigsen

[11] Patent Number: 5,236,664
[45] Date of Patent: Aug. 17, 1993

[54] APPARATUS FOR MONITORING BLOOD LOSS

[75] Inventor: Bernhard Ludvigsen, Mobile, Ala.

[73] Assignee: University of South Alabama, Mobile, Ala.

[21] Appl. No.: 861,102

[22] Filed: Mar. 31, 1992

Related U.S. Application Data

[63] Continuation-in-part of Ser. No. 681,896, Apr. 8, 1991.

[51] Int. Cl.$^5$ .............................................. A61B 5/00
[52] U.S. Cl. ...................................... 422/44; 422/20;
422/68.1; 422/82.03; 436/66; 128/638;
210/748; 356/40; 204/416
[58] Field of Search ...................... 436/66, 155, 177;
422/20, 44, 62, 82.03, 68.1; 128/637, 638;
435/2, 288; 210/646, 748; 356/40; 204/416

[56] References Cited

U.S. PATENT DOCUMENTS

| | | | |
|---|---|---|---|
| 3,492,095 | 1/1970 | Tillen | 23/230 |
| 3,874,850 | 4/1975 | Sorensen et al. | 356/40 X |
| 3,972,614 | 8/1976 | Johansen et al. | 356/40 X |
| 4,193,818 | 3/1980 | Young et al. | 422/128 X |
| 4,428,300 | 1/1984 | Tarcy | 436/124 X |
| 4,562,842 | 1/1986 | Morfeld et al. | 128/638 |
| 4,766,080 | 8/1988 | Fleming | 436/164 X |
| 4,773,423 | 9/1988 | Hakky | 128/637 |
| 4,853,338 | 8/1989 | Benezra et al. | 436/66 |
| 4,876,205 | 10/1989 | Green et al. | 436/66 |
| 5,087,379 | 2/1992 | Morton et al. | 210/748 |

Primary Examiner—James C. Housel
Assistant Examiner—Maureen M. Wallenhorst
Attorney, Agent, or Firm—Oblon, Spivak, McClelland, Maier & Neustadt

[57] ABSTRACT

A blood loss monitoring apparatus is disclosed. The system includes a tank having a solution which removes blood from blood containing materials which are deposited in the tank and also hemolyzes the blood. Blood and blood containing materials are deposited into the tank during surgery, and the volume of liquid in the tank as well as the hemoglobin concentration in the tank are then determined. From this information, the total amount of hemoglobin lost is determined, and by measuring the patient's hemoglobin level immediately prior to the surgery, the total amount of blood lost is then calculated. The amount of blood lost can be continuously monitored and updated throughout the course of the surgical procedure or operation.

20 Claims, 4 Drawing Sheets

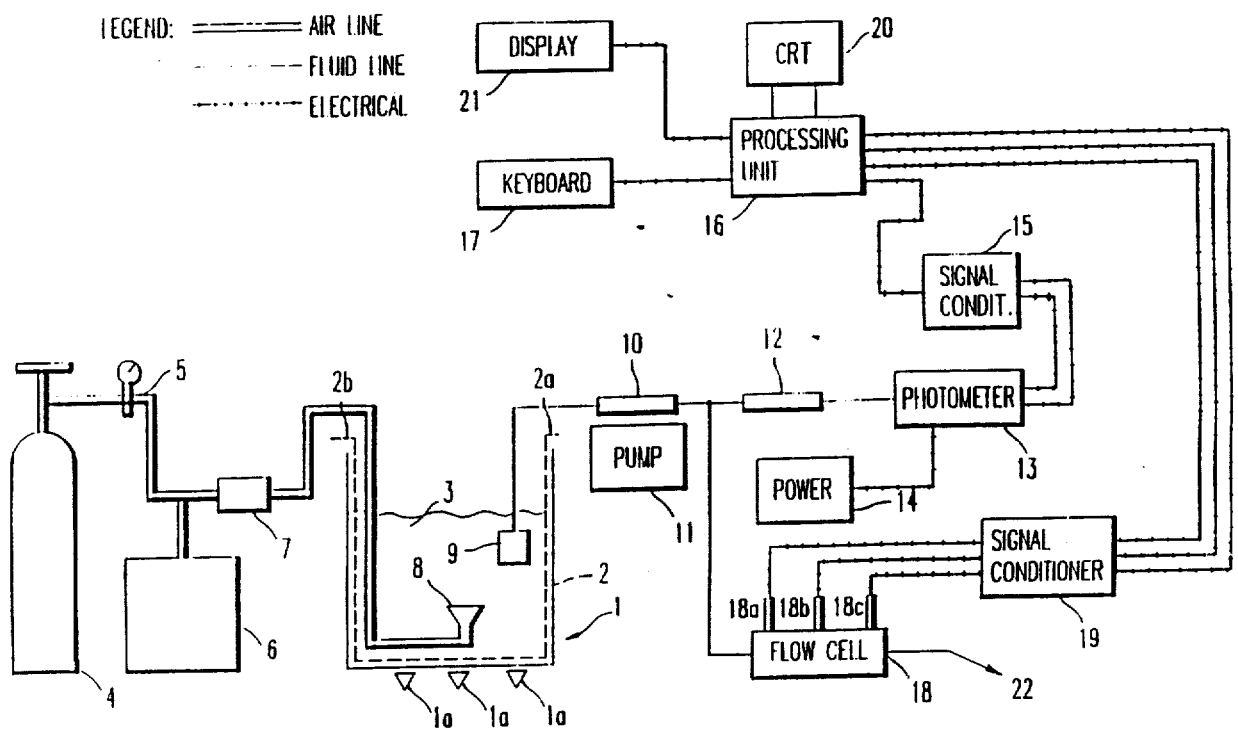

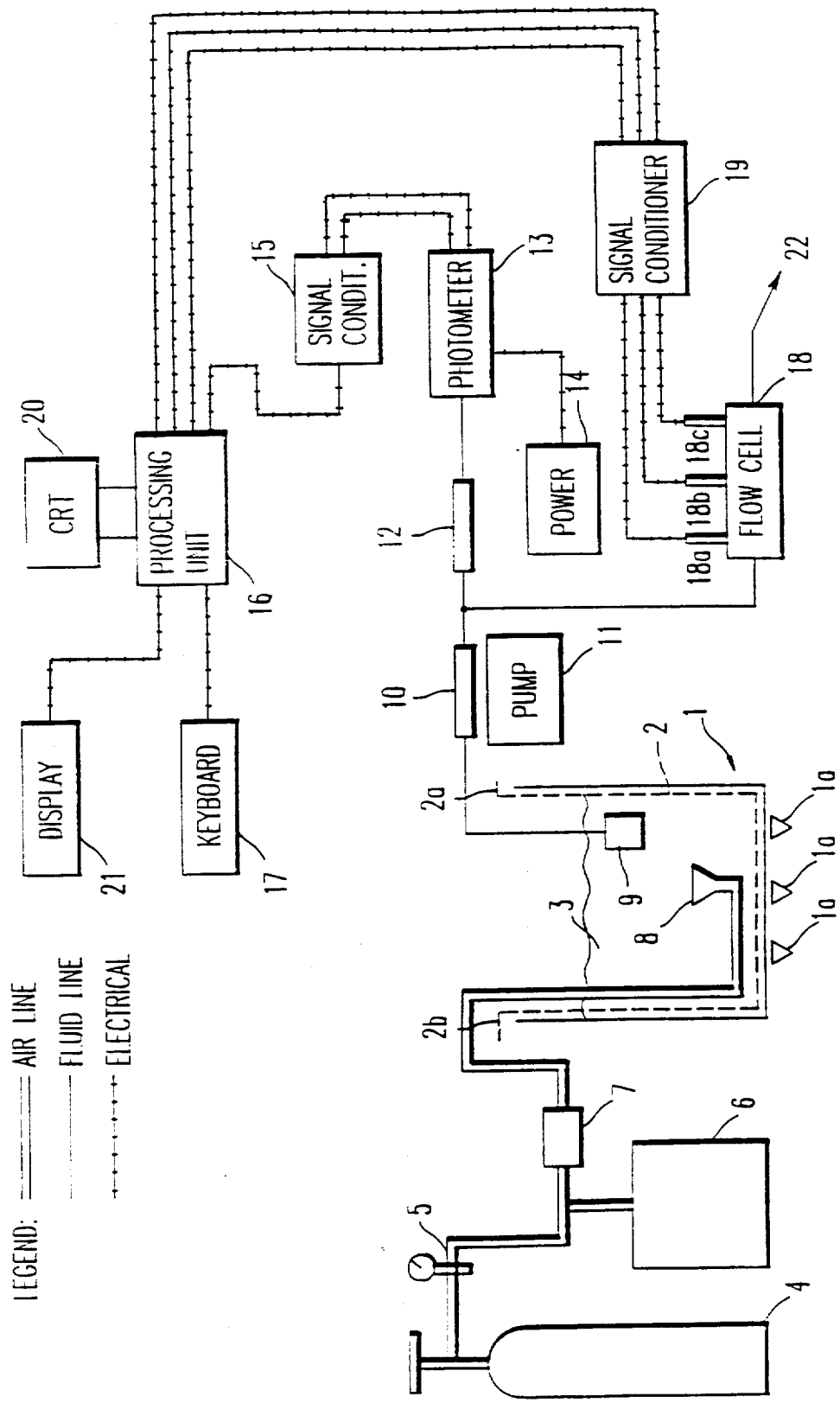

UNITED STATES PATENT AND TRADEMARK OFFICE
CERTIFICATE OF CORRECTION

PATENT NO. : 5,236,664  
DATED : August 17, 1993  
INVENTOR(S) : Bernhard Ludvigsen Page 1 of 2

It is certified that error appears in the above-indentified patent and that said Letters Patent is hereby corrected as shown below:

In the certificate of correctiondated May 2, 1995.

delete Drawing Sheet 2, and substitute therefor the Drawing Sheet consisting of FIG. 2, as shown on the attached page.

Signed and Sealed this

Eighth Day of August, 1995

Attest:

BRUCE LEHMAN

Attesting Officer

Commissioner of Patents and Trademarks